United States Patent
Levine (10) Patent No.: US 8,371,853 B2
(45) Date of Patent: Feb. 12, 2013

(54) MOUTHPIECE THAT ADJUSTS TO USER ARCH SIZES AND SEALS FROM OXYGEN EXPOSURE AND METHODS FOR EFFECTING AN ORAL TREATMENT

(75) Inventor: Jonathan B. Levine, Purchase, NY (US)

(73) Assignee: JBL Radical Innovations, LLCNY (US)

( * ) Notice: Subject to any disclaimer, the term of this patent is extended or adjusted under 35 U.S.C. 154(b) by 9 days.

(21) Appl. No.: 12/943,969

(22) Filed: Nov. 11, 2010

(65) Prior Publication Data

US 2011/0104633 A1     May 5, 2011

Related U.S. Application Data

(63) Continuation-in-part of application No. 12/246,012, filed on Oct. 6, 2008, now abandoned.

(51) Int. Cl.
*A61C 5/00*     (2006.01)
(52) U.S. Cl. .................... 433/215; 433/29; 433/32
(58) Field of Classification Search .............. 433/29, 433/32, 215
See application file for complete search history.

(56) References Cited

U.S. PATENT DOCUMENTS

| | | | |
|---|---|---|---|
| 5,702,250 A | 12/1997 | Kipke | ............. 433/37 |
| 6,155,832 A | 12/2000 | Wiesel | |
| 6,162,055 A | 12/2000 | Montgomery et al. | |
| 6,331,291 B1 * | 12/2001 | Glace et al. | .............. 424/49 |
| 6,616,451 B1 | 9/2003 | Rizolu et al. | |
| 6,620,405 B2 * | 9/2003 | Oxman et al. | .............. 424/45 |
| 6,623,272 B2 | 9/2003 | Clemans | |
| 6,733,290 B2 | 5/2004 | West et al. | .............. 433/29 |
| 6,752,627 B2 | 6/2004 | Lin | |
| 6,783,363 B2 | 8/2004 | Eguchi et al. | |
| 6,893,259 B1 * | 5/2005 | Reizenson | .............. 433/29 |
| 6,902,397 B2 | 6/2005 | Farrell et al. | |
| 7,004,756 B2 | 2/2006 | Andersen | |
| 7,086,862 B2 | 8/2006 | Craig | |
| 7,144,249 B2 | 12/2006 | Rizoin et al. | |
| 7,160,111 B2 | 1/2007 | Baughman | |
| 7,223,270 B2 | 5/2007 | Altshuler et al. | |
| 7,250,155 B2 | 7/2007 | Yamaguchi et al. | |
| 2003/0134253 A1* | 7/2003 | Hirsch et al. | .............. 433/93 |
| 2004/0193236 A1 | 9/2004 | Altshuler et al. | |
| 2005/0053898 A1 | 3/2005 | Ghosh et al. | |
| 2005/0064370 A1 | 3/2005 | Duret | |
| 2005/0074717 A1 | 4/2005 | Cleary et al. | .............. 433/24 |
| 2005/0158687 A1 | 7/2005 | Dahm | .............. 433/29 |
| 2005/0172429 A1 | 8/2005 | Russell et al. | |
| 2005/0202363 A1 | 9/2005 | Osterwalder | .............. 433/29 |
| 2005/0231983 A1 | 10/2005 | Dahm | .............. 362/800 |
| 2006/0019214 A1 | 1/2006 | Lawrence et al. | .............. 433/29 |

(Continued)

OTHER PUBLICATIONS http://www.exit15.com/briteteeth-laser-light-home-teeth-whitening "Sunshine Smiles Brite-Teeth Laser Light Home Teeth Whitening" p. 760 Nov. 15, 2007.

(Continued)

*Primary Examiner* — Cris L Rodriguez
*Assistant Examiner* — Eric Rosen
(74) *Attorney, Agent, or Firm* — H. Jay Spiegel (57) ABSTRACT

A mouthpiece that adjusts manually in the mouth and seals the treatment area. It includes light emitters and heat generators. Textured bands guide and direct light to diffuse evenly. A seal bead seals the gum above the teeth. For whitening, a whitening gel is first applied to the user's teeth, the mouthpiece is then positioned in the user's mouth, and the seal bead seals against the user's gums. Then, the light emitter(s) and heat generator(s) are activated to effect the whitening while causing an increase in the temperature enabling the user to mold the mouthpiece to their mouth.

37 Claims, 3 Drawing Sheets

U.S. PATENT DOCUMENTS

| | | |
|---|---|---|
| 2006/0078848 A1* | 4/2006 | Fischer et al. ............... 433/215 |
| 2006/0141422 A1 | 6/2006 | Philp, Jr. et al. |
| 2006/0194164 A1 | 8/2006 | Altshuler et al. |
| 2006/0257822 A1 | 11/2006 | Ghosh et al. |
| 2007/0003905 A1 | 1/2007 | Nguyen et al. ............... 433/215 |
| 2007/0009856 A1* | 1/2007 | Jones et al. .................. 433/215 |
| 2007/0015112 A1 | 1/2007 | Hochman et al. |
| 2007/0020584 A1 | 1/2007 | Madray |
| 2007/0259310 A1* | 11/2007 | Goodson et al. ............... 433/29 |
| 2007/0259316 A1* | 11/2007 | Conrad et al. ............... 433/215 |
| 2008/0003540 A1* | 1/2008 | Khawaled et al. ............ 433/215 |
| 2008/0032253 A1* | 2/2008 | Montgomery et al. ......... 433/29 |

OTHER PUBLICATIONS http://www.perfectlywhite.com/ "Welcome to Perfectly White.com (online since 2004)".

Smile Teeth Whitening Systems, 2005-2006 http://www.smileteeethwhitening.com/asupplies.html.

* cited by examiner

MOUTHPIECE THAT ADJUSTS TO USER ARCH SIZES AND SEALS FROM OXYGEN EXPOSURE AND METHODS FOR EFFECTING AN ORAL TREATMENT

REFERENCE TO RELATED APPLICATIONS

The present application is a continuation-in-part of U.S. patent application Ser. No. 12/246,012 filed Oct. 6, 2008, now abandoned and incorporated by reference herein.

BACKGROUND OF THE INVENTION

1. Field of the Invention

The present invention relates to a mouthpiece containing lamps to expose electromagnetic radiation to effect oral treatment and, specifically, to aid the activation of an adhesive whitening gel to whiten teeth. The present invention may also be used to kill harmful bacteria in the mouth through the electromagnetic radiation exposure. The mouthpiece adjusts manually to accommodate a broad range of user sizes, yet seals the treatment area from oxygen exposure.

The present invention relates generally to a method for effecting an oral treatment using a mouthpiece containing light and heat generating devices and more specifically, to a method for treating teeth by aiding in the activation of a gel applied to the teeth and that contains light and/or heat reactive compounds. Accordingly, the present invention relates to a method for whitening teeth, a method for treating gum disease by killing harmful bacteria in the mouth, a method for desensitizing teeth, a method for freshening breath, and a method for accelerating healing of oral sores or ulcers, all through the exposure of the teeth, targeted soft tissue and a specific gel applied thereto, to light and/or heat using a mouthpiece. In the methods, the mouthpiece is designed to adjust manually to accommodate a broad range of user sizes, and closes the system, thus sealing the treatment area from the actives escaping, i.e., oxygen, as well as to adjust during the oral treatment using muscles of the mouth.

2. Description of Related Art

Conventional teeth whitening in the dental office takes up to two hours, may be painful and is often costly with noticeable regression beginning in about seven days after the treatment. Improved whitening results are experienced in a professional setting using white light in the 300-990 nm range, but this procedure may be costly and time consuming. Over-the-counter products suffer from other deficiencies, such as difficulty of use, irritation to the fingers and results usually take seven to ten days. Often, there is only minimal improvement. The consumer needs a customizable whitening alternative that yields results similar to the initial professional whitening, but at the convenience of the home that allows for frequency applications and a more stabilized whitening result.

Dentist-supervised tooth whitening involves the controlled use of carbamide or hydrogen peroxide, tailored to a particular patient. Dentists may administer in-office treatments or at-home treatments. Before the tooth whitening treatment, most dentists clean the teeth, fill cavities, and ensure the patient's gums are healthy.

Most in-office tooth whitening systems use 15 to 35 percent hydrogen peroxide gels, sometimes coupled with a high intensity light to expedite the bleaching chemical reaction.

The in-office procedure involves the dentist gently cleaning the teeth with pumice and then applying a protective barrier on the gums. The dentist then applies hydrogen peroxide paste on the teeth for several minutes, rinses the hydrogen peroxide paste off, and usually reapplies the hydrogen peroxide paste several times. The procedure can achieve about four to six shades of whitening after only one 40-minute treatment.

At-home systems will often use 10 to 20 percent carbamide peroxide gels or up to 7 to 8 percent hydrogen peroxide that also contain glycerin, carbomer or carbamide, sodium hydroxide, water, and flavoring agents. Some gels that contain more than 10 percent carbamide peroxide will also include sodium fluoride to reduce sensitivity and strengthen teeth.

To begin the at-home procedure, the dentist takes impressions (molds) of the mouth, and then has soft, custom mouth trays made. In administering the treatment, the user places a thin ribbon of the gel into the tray and wears it for two hours during the day, or while sleeping. Most whitening occurs in one to two weeks. In difficult cases, trays may need to be worn for up to six weeks.

A combination of in-office and at-home systems can achieve up to 8 to 10 shades of whitening. Such a procedure is considered safe and effective when monitored by a dentist.

Dentist supervised systems have advantages and disadvantages when compared to over-the-counter tooth whitening products. The main advantage of the dentist supervised system is that the dentist can determine if tooth whitening should be performed and if it will be effective for the patient. Patients with decayed teeth, infected gums, white spots on their teeth, and multiple tooth colored fillings or crowns (caps) on the front teeth may not be good candidates for tooth whitening.

The dentist can also help decide what type of tooth whitening is required (in-office, at-home or both) and the concentration of the whitening gels. The dentist can monitor and treat patients who experience sensitivity to the whitening agents and modify the procedure for those who are having difficulty getting optimal results. Finally, the dentist can help the patient explore porcelain or resin veneers, tooth colored fillings, gum lifts and tooth shaping used with or without tooth whitening. With the help of the dentist, the patient's cosmetic dental goals may be more easily attained.

The disadvantages of dentist supervised whitening systems include higher cost and longer time required to get started when the professional whitening is used. Also, the whitening results will start to regress as early as seven days after the treatment. The in-office and at-home tooth whitening systems can cost between $300-$1,000 (sometimes more). In most cases, at-home systems cost less than the in-office systems. With the dentist supervised systems, there may be a wait to get started. You have to schedule an appointment, wait to be seen and evaluated, and then be treated.

Whitening results are best achieved when there is high frequency of use of the whitening agent, in a safe manner without high concentrations of whitening agents that can burn the gum tissue. By increasing the frequency of the whitening by giving the consumer the ability to whiten at home, the regression of the whitening is greatly reduced or even eliminated.

It is desired to provide a whitening method using a whitening device (mouthpiece) that is coupled with a delivery system of the whitening gel and an adhesive that keeps a photosensitive agent, such as carbamide or hydrogen peroxide, targeted to the area to be whitened, i.e. to the tooth surface. Such a whitening device preferably causes no harmful breakdown by-products, and is hygienically delivered in a single dose.

Further, it is desired to have a whitening method using an adjustable whitening device (mouthpiece) to accommodate a broad range of different size sets of upper or lower teeth of users. It is further desired that the whitening device seal off the area in the mouth to be treated to reduce the amount of oxygen exposure.

In addition, harmful bacteria responsible for causing gum disease in the mouth, specifically, the gram negative anaerobic bacteria, are killed by exposure to ultraviolet light. It would therefore be desirable for a consumer to expose such bacteria to ultraviolet light as well.

With respect to the need to desensitize teeth, tooth sensitivity occurs by the gingiva receding off of the tooth surface and thus exposing the root areas/surfaces of the tooth. These areas have small dentinal tubules that are filled with fluid that originate near the pulp of the tooth and are prone to excitation by certain stimuli of air and cold temperatures. A traditional method to desensitize teeth is to use a toothpaste or dentifrice that contains potassium nitrate and fluoride which seals the tubules and prevents the transmission of the stimulus to the root surface of the tooth.

It is desired to improve the traditional method to desensitize teeth. Even more generally, it is desired to improve the ability to treat teeth in various treatments using a mouthpiece that better conforms to the patient's mouth to thereby enhance the chemical reactions occurring on or around the teeth.

SUMMARY OF THE INVENTION

One aspect of the invention resides in an intra-oral whitening device or mouthpiece and a method for whitening teeth using the intra-oral whitening device or mouthpiece suited to create a whitening and heat effect to increase a reaction rate of a photosensitive agent, such as carbamide or hydrogen peroxide gel. The person whose teeth are to be whitened can wear the device and whiten his/her teeth without the need of a professional office in a safe, effective, convenient and economical fashion.

The intra oral whitening device (or mouthpiece) of the present invention allows whitening teeth in the convenience of one's home with LED-based white light technology and one or more heat resistors to customize the whitening procedure safely and effectively without the need for a dentist. The mouthpiece adjusts its orientation manually to accommodate a broad range of different size sets of upper or lower teeth of users and to seal a treatment area in the mouth against exposure to oxygen. The mouthpiece also adjusts during treatment as the mouthpiece is warmed by the presence of a heat source therein to enable the mouthpiece to the molded or shaped by the user's oral muscles, e.g., the orbicularis oris.

Another aspect of the invention is a method for exposing harmful bacteria in the mouth to ultraviolet light. By doing so, the spread of gum disease caused by the harmful bacteria, such as gram negative anaerobic bacteria, is halted because the ultraviolet light kills the harmful bacteria. Additionally, activated oxygenating compounds will also kill anaerobic gram negative bacteria that cause gum disease.

Yet another aspect of the invention is a method for desensitizing teeth by applying a substance containing fluoride and/or potassium nitrate to the teeth, and then utilizing the mouthpiece to generate light and heat thereby causing an increased uptake of fluoride ions and/or potassium nitrate which acts to seal the dentinal tubules.

Still another aspect of the invention is a method for freshening a patient's breath wherein a freshening gel is applied to the teeth, and then the mouthpiece is placed into the patient's mouth and activated to generate light and heat thereby activating light and/heat reactive compounds that kill the bacteria that cause bad breath.

Still another aspect of the invention is a method for accelerating healing of sores or ulcers in the mouth wherein a gel containing a compound that will provide such acceleration, e.g., one containing hydrogen peroxide, is applied to the teeth, and then the mouthpiece is placed into the patient's mouth and activated to generate light and heat thereby activating the healing-enhancing compound(s) in the gel, i.e., oxygenating agents, resulting in accelerated healing of the sores or ulcers.

Other aspects of the invention include methods for effecting other oral treatments wherein the application of light and/or heat to the teeth is needed. Accordingly, the present invention encompasses the application of a light and/or heat-reactive gel or similar compound, including the gels mentioned above, to teeth with the subsequent placement of the mouthpiece and activation of light and/or heat generators in the mouthpiece to effect an oral treatment.

BRIEF DESCRIPTION OF THE DRAWING

For a better understanding of the present invention, reference is made to the following description and accompanying drawings, while the scope of the invention is set forth in the appended claims:

DETAILED DESCRIPTION OF THE INVENTION

Described below is a device for use in an oral treatment and several oral treatments are explained in detail. The invention however is not limited to the oral treatments disclosed herein and encompasses the use of the device for any oral treatment wherein the application of light and/or heat to the oral cavity, e.g., to the teeth and/or gums, is needed. A first exemplifying use of the device is for whitening teeth.

During a teeth whitening treatment in a dental office, a whitening gel is applied to the teeth and a protective barrier is placed on the gums, the mucosa and lips to prevent burning of the tissues by the relatively high concentration of hydrogen peroxide in the whitening gel. A leading edge of the whitening gel is placed on a tooth surface. An LED-based white light is placed a few inches from such a tooth surface to help activate free radical oxygen, most of which becomes lost into the air. By contrast, in this invention, a mouthpiece is provided that seals or encloses a photosensitive agent, such as carbamide or hydrogen peroxide gel, to prevent the loss of the active electrons of the photosensitive agent (carbamide or hydrogen peroxide) into the air.

The mouthpiece holds at least one LED-based white light source, or other comparable light source(s), and preferably at least one heat generator, e.g., a heat resistor that generates heat in response to applied electric current. A power source, which may be remote from the mouthpiece, is in electrical connection with the LED-based white light source(s) via a wire, and the heat generator(s), via the same or different wires. The power source energizes the LED-based white light source(s), which generate light rays, and the heat generator(s), which generates heat. The light rays strike the tooth surface on the front and the edge and the back of the edge while the mouthpiece is in its intended position relative to the tooth surface.

Further, a "closed system" created by the mouthpiece or guard that seals or encloses (against exposure to the atmosphere) is efficient for keeping the active free radical oxygen in close proximity to the teeth to enable their movement onto the tooth surface to breakdown the color pigments inside the tooth. A much lower concentration of the carbamide or hydrogen peroxide gel may be used in comparison to what would be needed to achieve like results in an "open system" that did not seal or enclose the photosensitive agent (carbamide or hydrogen peroxide) from exposure to atmosphere.

Indeed, the whitening device (mouthpiece) of the present invention may be used for seven to ten consecutive days with little to no sensitivity to the teeth and gums. This seven to ten consecutive day use constitutes a higher frequency of use than is available in conventional professional whitening techniques and helps avoid a regression phenomenon that has been observed in the professional whitening technique.

Referring now to the drawings, the mouthpiece 10 adjusts to a broad range of user dental arch sizes (curvature attributed to lower or upper sets of teeth). It also distributes light and heat in a controlled and focused fashion and provides a means of sealing an area being treated from exposure to oxygen.

Figure 1:
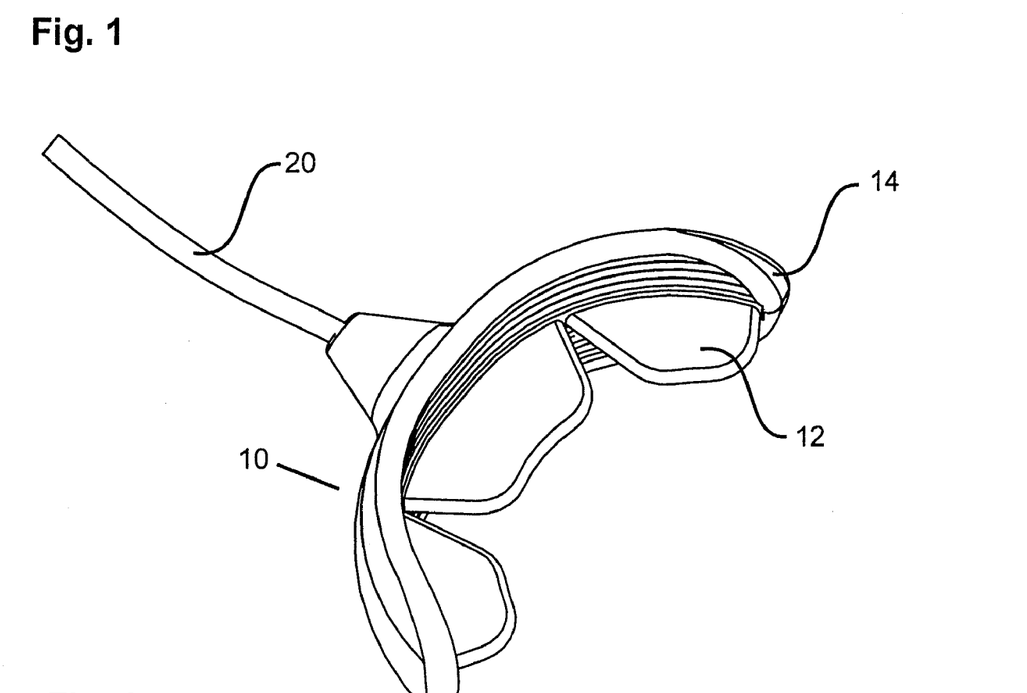
FIG. 1 is an isometric view of a dental mouthpiece in accordance with the invention.
Figure 3:
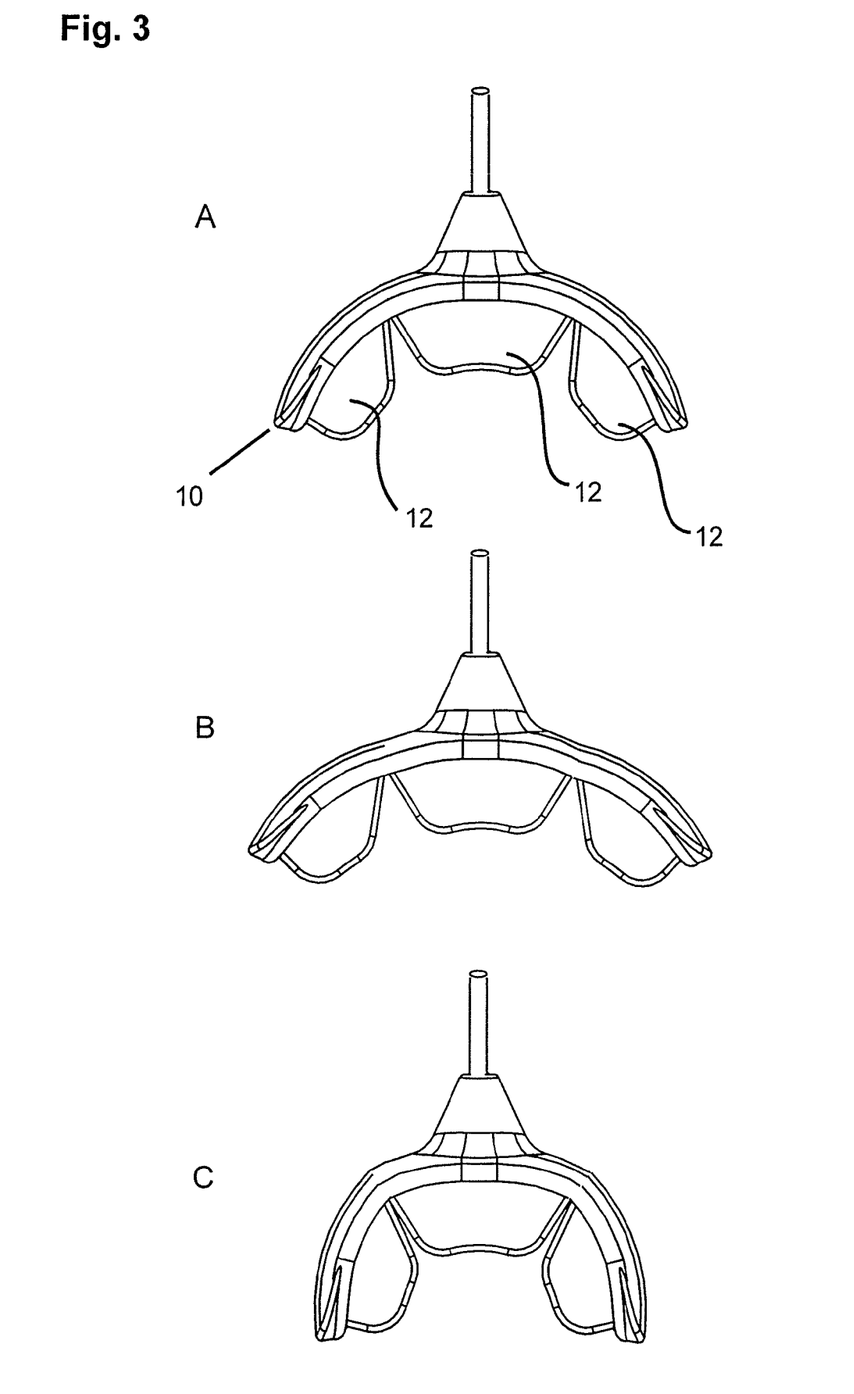
FIGS. 3A, 3B and 3C are top views of the dental mouthpiece of FIG. 1 that illustrate how the dental mouthpiece is adjusted to open from the position reflected by FIG. 3A to that of FIG. 3B and to close from the position reflected by FIG. 3A to that of FIG. 3C.

Referring to FIG. 1, the mouthpiece 10 includes a bite surface 12 formed of segments. The bite surface 12 is central and perpendicular to the main body 14, and thus extends outward from a central portion of the inner surface of the main body 14, on one side thereof. Generally, the bite surface 12 is configured to ensure stability of the mouthpiece 10 when positioned in the user's mouth between the upper and lower arches. As shown, the bite surface 12 is formed from three segmented or separated portions to thereby enable the main body 14 to be bent to conform to the size of the user's mouth and provide the separated bite surface portions with different configurations without overlap of any adjacent bite surface portions. Three such configurations are shown in FIGS. 3A, 3B and 3C. The number of bite surface portions may be different than the three as in the illustrated embodiment.

Figure 2:
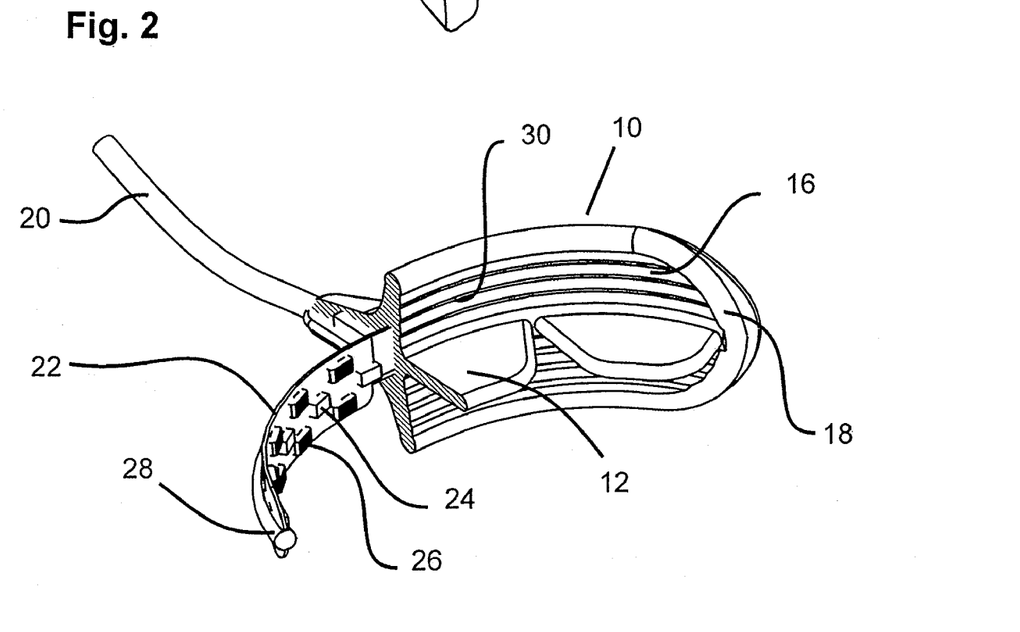
FIG. 2 is a partially broken isometric view of the dental mouthpiece of FIG. 1.

Referring to FIG. 2, the mouthpiece 10 is preferably formed of a clear, elastomeric, molded main body or outer shape 14 that encases a flexible circuit board 22. There is a deformable frame 28 that holds the circuit board 22 during fabrication and may be bent by the user to adjust the orientation of the mouthpiece 10 to set the arch for comfort in the user's mouth.

A series of super bright light emitting diodes (LEDs) 24 and heat generators, namely, heat generating resistors 26, are arrayed on the flexible circuit board 22, at least the LEDs 24 on an inner, lingual side thereof. A power cord 20 is centrally attached to the outer surface and enables power to be provided to the LEDs 24 and the heat generating resistors 26. It is envisioned that in some embodiments of the invention, the flexible circuit board 22 includes only a single light emitting diode or other light generating component, and a plurality of light emitting diodes are not present. Similarly, it is envisioned that in some embodiments of the invention, the flexible circuit board 22 includes only a single heat generator, and a plurality of heat generators are not present. Moreover, the heat generating resistors 26 exemplify a heat generator or source inside of the mouthpiece 10 and different components that generate heat from within the mouthpiece 10 to enable the mouthpiece 10 to be warmed and deformed are also envisioned to be within the scope and spirit of the invention.

A parallel series of textured bands 16, whose surface texture resembles elongated convex surfaces configured to channel LED light, are formed on the lingual side of the main body 14 for the purposes of LED light diffusion over the surface of the tooth being treated. The textured bands are a form of guided-light optics (GLO) in that they guide or channel light from a source to a desired area of application at which the light causes a reaction of chemicals for a beneficial purpose, in accordance with the invention. Other techniques to guide light from a source to a treatment area are also envisioned within to be within the scope and spirit of the invention.

Referring to FIG. 3A, areas between the segmented bite surface 12 allow the device to open as in FIG. 3B or close as in FIG. 3C.

Figure 4:
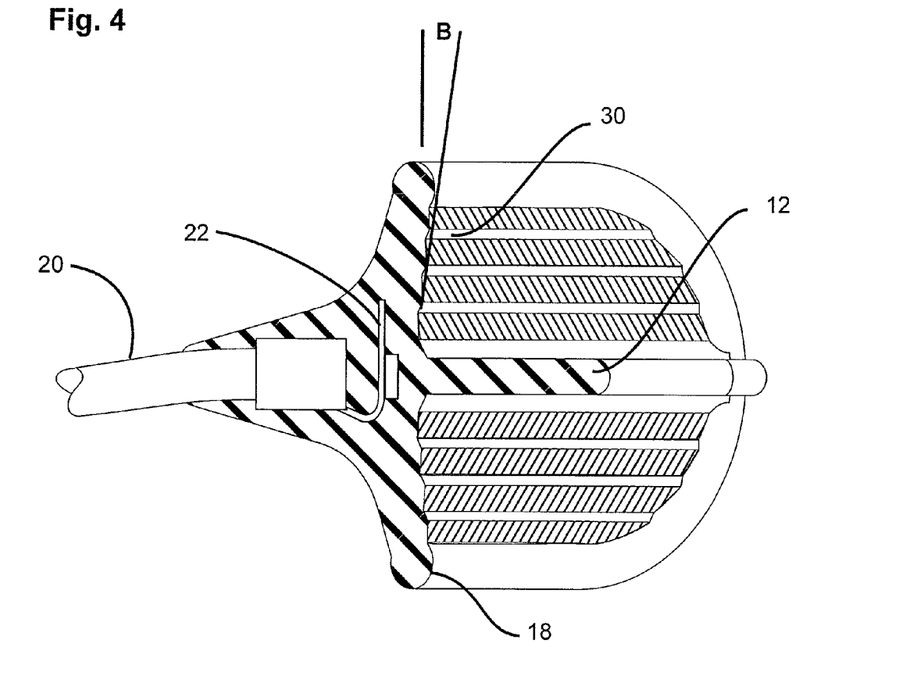
FIG. 4 is a cross-section through a centerline of the dental mouthpiece of FIG. 1.

Referring to FIG. 4, an inner surface 30 of the mouthpiece 10 above the bite surface 12 tilts inward at an angle of about 5 to about 15 degrees as noted by B to seal the upper seal bead 18 and borders the upper edge of the mouthpiece 10. Similarly, an inner surface of the mouthpiece 10 below the bite surface 12 may tilt inward at an angle of about 5 to about 15 degrees to seal the lower seal bead 18 and borders the lower edge of the mouthpiece 10. The angle for the upper and lower surfaces may be the same or different. The seal beads 18 provide the mouthpiece 10 with rolled and beaded outer edges that form, when the mouthpiece 10 is positioned in the user's mouth against the user's gums, a seal around the mouthpiece 10.

Figure 5:
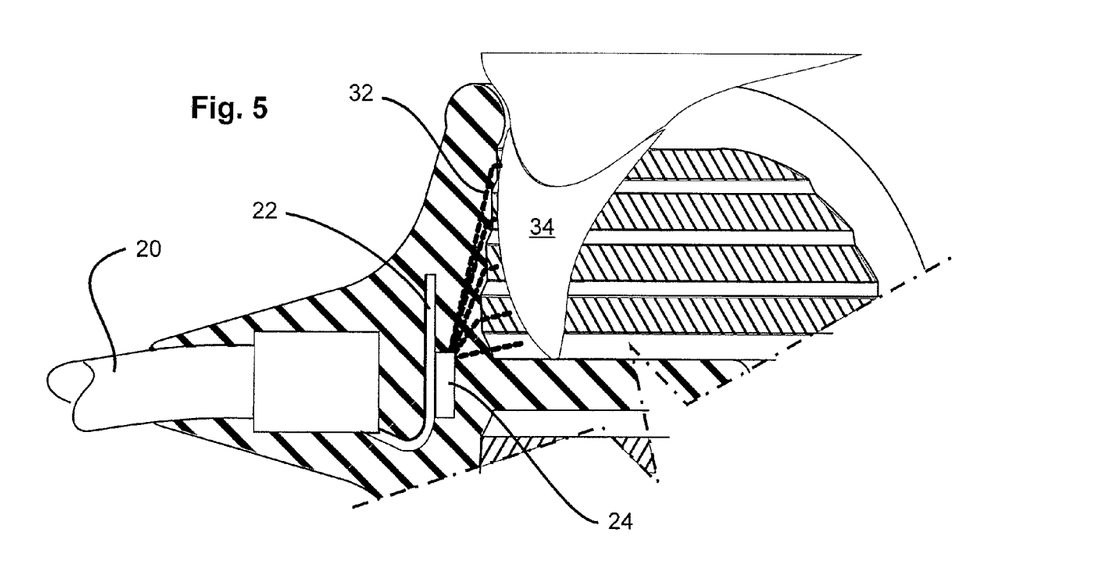
FIG. 5 is cross-section of the dental mouthpiece of FIG. 1 with respect to a user's tooth.

Referring to FIG. 5, the inward tilt of the inner surface 30 above the bite surface 12 allows the seal bead 18 to contact the gum above the teeth 34. This contact provides a barrier seal to both retain the whitening gel and to prevent active oxygen from escaping from the treatment area of the tooth (e.g., that area being treated with the whitening gel). The same effect is provided by the inward tilt of the inner surface below the bite surface 12 to the gum below the teeth.

In use, the light 32 emitted by the LEDs 24 is guided using a GLO technique, such as the textured bands 16, and directed to more evenly illuminate the surface of the teeth 34 by the textured bands 16. The texture of the textured bands 16 provides surfaces that are closer to perpendicular to the light path and less reflective than the generally polished surface of the mouthpiece 10.

The mouthpiece 10 may be used in various methods for effecting an oral treatment, usually to treat teeth against which the mouthpiece is placed such as by whitening the teeth as mentioned above. In a typical oral treatment, the presence of the electrically activated light emitters, i.e., LEDs 24; and heat generators, i.e., heat generating resistors 26, is utilized. The mouthpiece 10 would be positioned in the user's mouth such that the bite surface 12 is between an upper arch and a lower arch and the main body 14 is between a front surface of the teeth and an inner surface of the user's lips. Then, the light emitters and heat generators are electrically activated to effect the oral treatment. To improve the treatment, it would be beneficial for the user to bite down on the bite surface 12 to secure the mouthpiece 10 in their mouth and only thereafter activate the light emitters and heat generators.

When the oral treatment is tooth whitening, a whitening gel would be applied to the user's teeth prior to positioning the mouthpiece 10 in the user's mouth. As noted above, the inwardly tilting inner surfaces of the main body 14 of the mouthpiece causes the seal beads 18 that border an outer edge of the mouthpiece 10 to provide a barrier seal to retain the whitening gel. Thus, when the whitening gel contains hydrogen peroxide, the barrier seal effectively prevents oxygen from escaping an area of the teeth being treated by the hydrogen peroxide-containing whitening gel thereby improving the tooth whitening procedure. Accordingly, it is desired to position the seal beads 18 that are around the outer edge of the mouthpiece 10 against gums of the user (see FIG. 5).

To further improve the oral treatment, the mouthpiece is designed to be anatomically shaped individually for each user. Initially, the main body 14 may be bent via the deformable frame 28 (see FIGS. 3A, 3B and 3C) Thereafter, during treatment when the user is biting down on the bite surface 12, the mouthpiece 10 can adjust to the user because the heat generating resistors 26 generate heat that warms up material of the main body 14, e.g., medical grade silicone. At this time, the orbicularis oris muscle of the mouth exerts pressure to mold or shape the now malleable main body 14 to conform to the user's mouth. The bite surface 12, which may also be formed of medical grade silicone or other comparable material, can also be molded once it is warmed up by the activity of the heat generating resistors 26 A customized fit for the mouthpiece 10 to the user is thereby provided. In addition to or instead of medical grade silicone, bite surface 12 and the main body 14 may be formed of any plasticized material that warms and deforms, i.e., when subjected to heat generated by the heat generating resistors 26, and ideally maintains its molded form, i.e., after the heat has ceased. Thus, the bite surface 12 and main body 14 will ideally have thermoplastic characteristics. In this manner, during the initial use, the patient would shape the mouthpiece 10 to their mouth, but for subsequent uses, the mouthpiece 10 would maintain that form and shaping would not be substantially required.

The whitening method using mouthpiece 10 provides advantages over prior art whitening techniques, some of which are described above. In an exemplifying professional whitening procedure, a light source is positioned about three inches from the teeth to which the whitening gel has been applied. As a result, only the leading edge of the gel is functioning to whiten the teeth, while the rest of the whitening gel, which breaks down into water and highly reactive oxygen, goes into the atmosphere because the treatment area is not sealed. This type of professional procedure therefore requires about 4 twenty-minute treatments. A consequence of this procedure is a large degree of sensitivity of the teeth, often referred to as zingers. By contrast, use of the mouthpiece 10 in a whitening procedure in accordance with the invention is significantly more efficient taking less time and with less negative consequences to the user because reactive oxygen is prevented from escaping from the treatment area by the incorporation of the light emitting and heat generating systems within the mouthpiece 10 and the presence of the rolled and sealed bead edges 18 formed at the outer edges of the mouthpiece 10.

Mouthpiece 10 may therefore be used in a method for whitening teeth performed in a home setting allowing a user to whiten their teeth several times in a row spread out over a single day or several days. Moreover, a lower concentration whitening gel, e.g., a 6% to 10.2% whitening hydrogen peroxide gel, may be used for these multiple treatments over several days in a row, in comparison with whitening procedures at dentist's offices wherein an 18% hydrogen peroxide gel is typically used a single time.

Mouthpiece 10 may also be used in a method to desensitize teeth. In a method for desensitizing teeth using mouthpiece 10, in accordance with the invention, a substance containing fluoride and/or potassium nitrate is applied to the teeth, and then the person puts the mouthpiece 10 into their mouth and activates the LEDs 24 and heat generating resistors 26. When activated by light and heat generated by the LEDs 24 and heat generating resistors 26, in the manner described above, the substance causes an increased uptake of fluoride ions and/or potassium nitrate which acts to seal the dentinal tubules. Today, fluoride and potassium nitrate are used in toothpaste to help prevent root sensitivity. However, the user has to brush with this dentifrice multiple times to see a long term effect. With the mouthpiece 10 in combination with this substance, the efficacy of the uptake of these actions is greatly enhanced with the user seeing a much quicker response to desensitizing the root surfaces. The substance can be in the form of a liquid or a gel that can have thixotropic properties that allows for the targeting of the substance onto the exposed root surface with the light and/or heat of the mouthpiece 10.

Mouthpiece 10 may also be used in a method to accelerate healing of sores or ulcers in the mouth. In such a method, a gel containing a compound that will provide such acceleration, e.g., one containing hydrogen peroxide, is applied to the teeth, and then the mouthpiece 10 is placed into the patient's mouth and activated to generate light and heat, as discussed above, thereby activating the healing-enhancing compound (s) in the gel resulting in accelerated healing of the sores or ulcers. One factor causing the accelerated healing is the better retention of the compounds in the mouth resulting from the ability of the mouthpiece 10 to be warmed and deformed in the patient's mouth which improves the sealing of the mouthpiece 10 to the patient's mouth.

Mouthpiece 10 may also be used in a method for treating gum disease. In such a method, a gel is applied to the gums, the mouthpiece 10 is placed into the patient's mouth and activated to generate light, as discussed above. Harmful bacteria responsible for causing gum disease in the mouth, specifically, the gram negative anaerobic bacteria, are killed by exposure to the light and the active oxygens.

Mouthpiece 10 may also be used in a method for freshening a patient's breath. In this method, a freshening gel is applied to the teeth, and then the mouthpiece is placed into the patient's mouth and activated to generate light and heat thereby activating light and/heat reactive compounds in the gel resulting in breath freshening.

While the foregoing description and drawings represent the preferred embodiments of the present invention, it will be understood that various changes and modifications may be made without departing from the spirit and scope of the present invention.

What is claimed is:

1. A mouthpiece, comprising:
a main body; and
a bite tab that extends rearward from central of the main body and has an upper surface configured to be engaged by upper teeth of a user and a lower surface configured to be engaged by lower teeth of a user;
said main body being configured to bend under manual force to adjust an orientation of the main body to define an arch configuration; and
said main body containing an array of light emitters in a common plane with said bite tab that emit light and a first array of heat generators above said array of light emitters and a second array of heat generators below said array of light emitters, said heat generators generating heat when activated, whereby when said mouthpiece is received in a mouth of a user and said arrays are activated, said arrays expose regions of said mouth above and below said bite surface to heat and light, activation of said arrays of heat generators causing said main body to be heated and thereby become malleable allowing the main body to be molded to conform to the mouth of the user, wherein the main body maintains its molded configuration after said arrays of heat generators are deactivated.

2. The mouthpiece of claim 1, wherein the main body includes a deformable frame holding a flexible circuit board, the array of light emitters and the arrays of heat generators being arranged on the flexible circuit board.

3. The mouthpiece of claim 2, wherein the main body encases the flexible circuit board, the array of light emitters and the arrays of heat generators being on a lingual side of the flexible circuit board.

4. The mouthpiece of claim 2, further comprising a power cord attached to a central region of an outside facing surface of the flexible circuit board.

5. The mouthpiece of claim 1, further comprising a parallel series of textured bands on a lingual side of the main body to diffuse light from the array of light emitters toward areas to be treated.

6. The mouthpiece of claim 5, wherein the mouthpiece includes a polished surface, the textured bands being arranged to guide and direct the light from the array of light emitters so as to more evenly illuminate surfaces of the teeth than would otherwise be the case without the textured bands being present, the textured bands having a surface texture that is closer to being perpendicular to a path of the light and less reflective than the polished surface of the mouthpiece.

7. The mouthpiece of claim 1, wherein said main body includes a deformable frame, and further wherein the bite tab is segmented into a plurality of spaced apart segments that allow room for the deformable frame to flex to selectively re-orient a configuration of the main body between open and closed positions.

8. The mouthpiece of claim 1, wherein the mouthpiece has an inner surface that inwardly tilts within an angular range of 5 to 15 degrees to seal a seal bead, which borders an edge of the mouthpiece.

9. The mouthpiece of claim 8, wherein the inner surface inwardly tilts to allow the seal bead to contact a gum above a tooth, the contact providing a barrier seal to both retain a whitening gel and to prevent oxygen from entering an area of the tooth to be treated by the whitening gel.

10. A method for effecting an oral treatment, comprising:
providing a mouthpiece including one array of light emitters and first and second arrays of heat generators located above and below said array of light emitters, respectively, the mouthpiece having a main body and a bite tab that extends rearward from central of the main body, the array of light emitters being coplanar with said bite tab;
positioning the mouthpiece in a user's mouth such that the bite tab is between an upper arch and a lower arch and the main body is between a front surface of the user's teeth and an inner surface of the user's lips; and
activating the array of light emitters and arrays of heat generators to effect the oral treatment above and below said bite surface, further wherein the main body and bite surface contain a thermoplastic material, further comprising configuring the thermoplastic material-containing main body and bite surface to warm up when the arrays of heat generators are activated thereby causing the main body and bite surface to become malleable to enable the main body and bite surface to be molded by the user during the oral treatment to conform to the mouth of the user, and wherein the main body maintains its molded configuration after said arrays of heat generators are deactivated.

11. The method of claim 10, wherein the oral treatment is tooth whitening, further comprising applying a whitening gel to the user's teeth prior to positioning the mouthpiece in the user's mouth.

12. The method of claim 11, wherein the mouthpiece has an inner surface, further comprising configuring the inner surface to inwardly tilt within an angular range of 5 to 15 degrees to seal a seal bead that borders an outer edge of the mouthpiece and thereby provide a barrier seal to retain the whitening gel.

13. The method of claim 11, wherein the whitening gel contains hydrogen peroxide and a barrier seal on the mouthpiece prevents oxygen from escaping from an area of the teeth being treated by the hydrogen peroxide-containing whitening gel.

14. The method of claim 10,
wherein the mouthpiece further comprises a seal bead around an outer edge of the mouthpiece; and
wherein the method further comprises positioning the seal bead against gums of the user,
the array of light emitters and arrays of heat generators being electrically activated only after the seal bead is positioned against the user's gums.

15. The method of claim 10, further comprising anatomically shaping the mouthpiece to conform to the user's gums by adjusting a deformable frame within said main body.

16. The method of claim 10, further comprising providing the mouthpiece with a rolled and beaded outer edge, the rolled and beaded outer edge providing, when the mouthpiece is positioned in the user's mouth against the user's gums, a seal around the mouthpiece.

17. The method of claim 10, wherein the bite tab is perpendicular to the main body and extends outward from a central portion of the main body.

18. The method of claim 10, wherein the bite tab comprises a plurality of separated portions to thereby enable the main body to bend to conform to the user's mouth; the plurality of separated portions having different configurations without overlap of any adjacent ones of the plurality of separated portions.

19. The method of claim 10, wherein the oral treatment is tooth desensitizing, further comprising applying a desensitizing gel containing at least one of the group consisting of fluoride and potassium nitrate to at least one of the user's teeth prior to positioning the mouthpiece in the user's mouth, activation of the array of light emitters and the arrays of heat generators when the mouthpiece is positioned in the user's mouth causing increased uptake of fluoride ions and/or potassium nitrate to seal at least one dentinal tubule.

20. The method of claim 19, wherein the at least one of the group consisting of fluoride and potassium nitrate is in thixotropic condition.

21. The method of claim 10, wherein the oral treatment is treatment for gum disease, further comprising applying a gel to the user's gum prior to positioning the mouthpiece in the user's mouth that treats gum disease, the array of light emitters and the arrays of heat generators being activated to cause bacteria that cause gum disease to die.

22. The method of claim 10, wherein the oral treatment is breath freshening, further comprising applying a breath freshening gel to the user's teeth prior to positioning the mouthpiece in the user's mouth, the array of light emitters and the arrays of heat generators being activated to cause bacteria that cause bad breath to die.

23. The method of claim 10, wherein the oral treatment is accelerated healing of oral sores or ulcers, further comprising applying a gel to the sores or ulcers prior to positioning the mouthpiece in the user's mouth.

24. A method for treating teeth of a user, comprising:
providing a mouthpiece including an array of electrically activated light emitters and first and second arrays of heat generators located above and below said array of light emitters, respectively, the mouthpiece having a main body having a seal bead around an outer edge and a bite tab that extends rearward from central of the main body, the array of light emitters being coplanar with said bite tab;
applying a gel to the user's teeth that contains at least one of the group consisting of light reactive compounds and heat reactive compounds; then
positioning the mouthpiece in the user's mouth such that the bite tab is between an upper arch and a lower arch, the main body is between a front surface of the user's teeth and an inner surface of the user's lips, and the seal bead is against gums of the user; and
electrically activating the array of light emitters and activating the arrays of heat generators to effect oral treatment above and below said bite surface while causing an increase in the temperature of the main body thereby causing the main body to become malleable, thereby enabling the user to mold the main body and conform a shape of the main body to their mouth, and wherein the main body maintains its molded configuration after said arrays of heat generators are deactivated.

25. The method of claim 24, wherein the mouthpiece has an inner surface, further comprising configuring the inner surface to inwardly tilt within an angular range of 5 to 15 degrees to seal the seal bead and thereby provide a barrier seal to retain the whitening gel.

26. The method of claim 24, wherein the gel is a whitening gel that contains hydrogen peroxide and a barrier seal on the mouthpiece prevents oxygen from escaping from an area of the teeth being treated by the hydrogen peroxide-containing whitening gel.

27. The method of claim 24, wherein the main body comprises a deformable frame, wherein the method further comprises anatomically shaping the mouthpiece to conform to the user's gums when positioning the mouthpiece in the user's mouth by adjusting the deformable frame.

28. The method of claim 24, wherein the bite tab comprises a plurality of separated portions to thereby enable the main body to bend to conform to the user's mouth; the plurality of separated portions having different configurations without overlap of any adjacent ones of the plurality of separated portions.

29. The method of claim 24, wherein the oral treatment is tooth desensitizing and the gel is a desensitizing gel containing at least one of the group consisting of fluoride and potassium nitrate, activation of the array of light emitters and the arrays of heat generators when the mouthpiece is positioned in the user's mouth causing increased uptake of fluoride ions and/or potassium nitrate to seal at least one dentinal tubule.

30. The method of claim 29, wherein the at least one of the group consisting of fluoride and potassium nitrate is in thixotropic condition.

31. The method of claim 24, wherein the oral treatment is treatment for gum disease, the array of light emitters and the arrays of heat generators being activated to cause bacteria that cause gum disease to die.

32. The method of claim 24, wherein the oral treatment is breath freshening, the array of light emitters and the arrays of heat generators being activated to cause bacteria that cause bad breath to die.

33. The method of claim 24, wherein the oral treatment is accelerated healing of oral sores or ulcers.

34. A method for creating a closed oral treatment system with a customized fit, comprising:
providing a deformable mouthpiece having an array of electrically activated light emitters and first and second arrays of electrically activated heat generators located above and below said array of light emitters, respectively;
said mouthpiece comprising a main body and a bite tab that extends rearward from central of the main body and has an upper surface configured to be engaged by upper teeth of a user and a lower surface configured to be engaged by lower teeth of said user;
positioning the mouthpiece in said user's mouth with a quantity of hydrogen peroxide within said mouthpiece; and
electrically activating the array of light emitters and the arrays of heat generators to cause the mouthpiece to be malleable by the user such that the mouthpiece molds and conforms to the user's mouth to enable the user to form a seal proximate to the user's teeth such that free radical oxygen from said hydrogen peroxide remains in close proximity to the user's teeth, and wherein the main body maintains its molded and conformed configuration after said arrays of heat generators are deactivated, said array of light emitters being coplanar with said bite tab.

35. The method of claim 34, wherein at least a portion of the mouthpiece is made of thermoplastic material.

36. The method of claim 34, wherein the main body has a seal bead around an outer edge of the main body, the mouthpiece being positioned in the user's mouth such that the bite tab is between an upper arch and a lower arch, the main body is between a front surface of the user's teeth and an inner surface of the user's lips, and the seal bead is against gums of the user.

37. The method of claim 36, wherein the arrays of heat generators are arranged in the main body to thereby cause the main body to warm up when the arrays of heat generators are activated.

* * * * *